United States Patent
Watson et al.

[11] Patent Number: 5,383,843
[45] Date of Patent: Jan. 24, 1995

[54] AIR PRESSURE KNEE BRACE APPARATUS

[76] Inventors: Randy C. Watson, 599 Lake Tahoe Blvd., Aspen Bldg. Suite B-1, South Lake Tahoe, Calif. 96150; Richard L. Baiocchi, 630 Alma Way, Zephyr Cove, Nev. 89448

[21] Appl. No.: 206,619

[22] Filed: Mar. 7, 1994

[51] Int. Cl.⁶ .................................................. A61F 5/00
[52] U.S. Cl. .................................. 602/13; 602/26; 2/22; 2/24; 2/DIG. 3; 128/DIG. 20
[58] Field of Search ............... 602/5, 6, 13, 19, 23, 602/26; 128/DIG. 20; 2/16, 22, 24, DIG. 3; 601/151; 273/189 R, 189 A; 607/108-112

[56] References Cited

U.S. PATENT DOCUMENTS

| | | | |
|---|---|---|---|
| 3,463,147 | 8/1969 | Stubbs | 2/24 X |
| 4,150,442 | 4/1979 | Boone | 2/24 X |
| 4,201,203 | 5/1980 | Applegate | 2/24 X |
| 4,250,578 | 2/1981 | Barlow | 2/24 |
| 4,624,248 | 11/1986 | Poole et al. | 601/151 |
| 5,031,240 | 7/1991 | Nierhaus | 2/24 |

*Primary Examiner*—Richard J. Apley
*Assistant Examiner*—Linda C. M. Dvorak
*Attorney, Agent, or Firm*—Thomas N. Neiman

[57] ABSTRACT

The novel air pressure knee brace apparatus is comprised of a unit that is capable of allowing the user to provide the amount of support pressure that he or she desires for the knee joint. The apparatus is comprised of a flexible material wrap that is designed to fit around the knee of an individual. The rear portion of the wrap can be made of a mesh material that permits a cooling of the leg area. The frontal portion of the material contains an air bladder retained in position by a mesh perimeter and overlay and contains an air valve that can be inflated as desired to provide the needed support for the knee joint and, at the same time, allow for freedom of motion of the knee joint. Adjustment units are attached to the apparatus to permit tightening or loosening of the entire apparatus around the leg.

6 Claims, 1 Drawing Sheet

U.S. Patent    Jan. 24, 1995    5,383,843
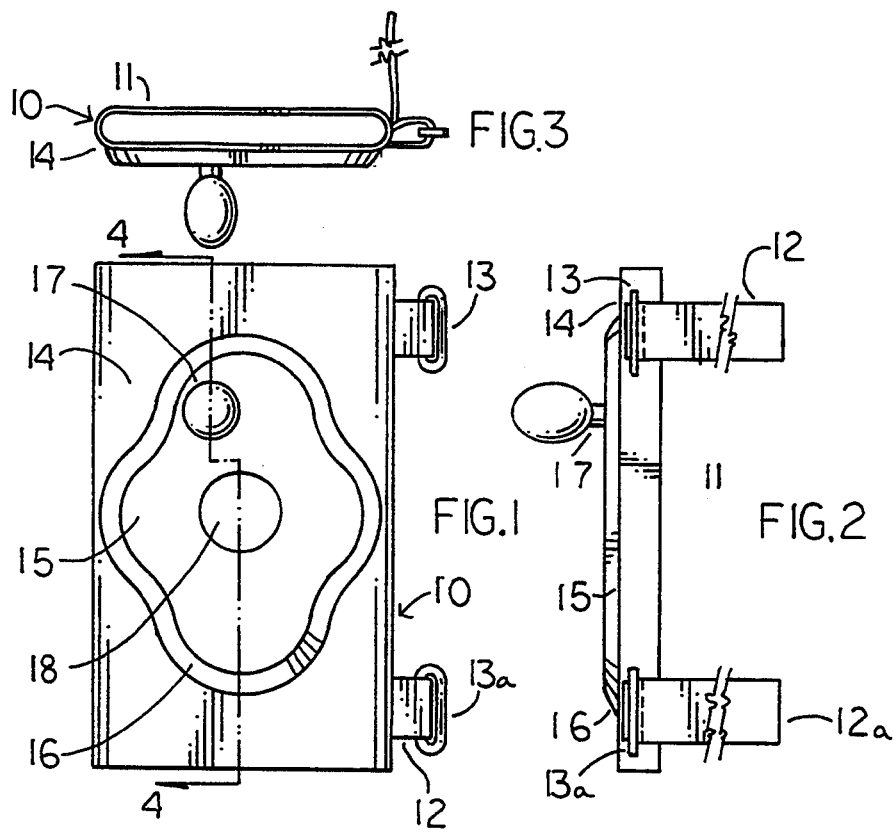
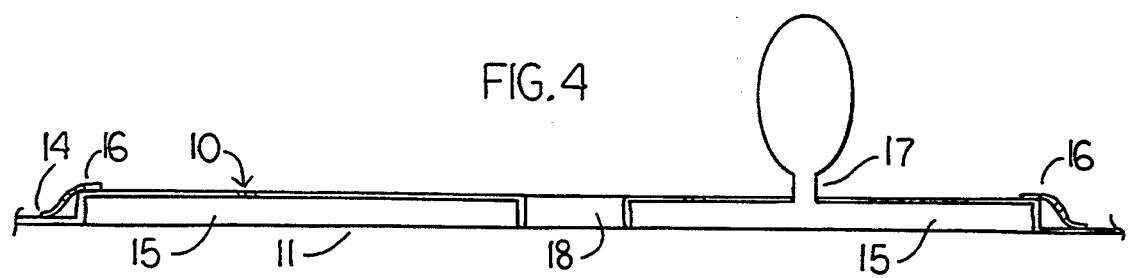

5,383,843

AIR PRESSURE KNEE BRACE APPARATUS

BACKGROUND OF THE INVENTION

This invention pertains to joint support devices, and, in particular, to an air pressure knee brace apparatus which allows the user to protect and support the knee with the amount of pressure that the individual can set by himself or herself.

Many types and designs of knee braces are currently on the market. There have been many different devices that have been patented. Examples of these tripods include the U.S. Pat. No. 4,700,698 to Horst Kleylein for a Knee Orthosis, issued on Oct. 20, 1987 and the United States Patent issued to Oris E. Harper, U.S. Pat. No. 4,425,912 for a Knee Protector/Stabilizer issued on Jan. 17, 1984. Both of these devices are knee support devices that have a stretchable material which surrounds the knee and a different number of means to tighten the device as necessary, but neither these devices, nor other references show a device which has a pre-determined shaped annular unit surrounding the kneecap or patella and can simply have the pressure in the annular pad changed as desired. What is needed is a lightweight support that an individual can easily fold and store and, at the same time, be readily accessible for use quickly and simply.

Clearly, it is desirable for a device of this type to be very lightweight and flexible. At the same time, the device should be easy to manufacture and be produced of inexpensive material. It is an object of this invention to set forth an air pressure knee brace apparatus which avoids the disadvantages, previously mentioned limitations of typical knee braces.

SUMMARY OF THE INVENTION

Particularly, it is the object of this invention to set forth an air pressure knee brace apparatus, for use in providing a lightweight protection and support unit for individuals desiring this protection and support, comprising flexible means; said flexible means comprising a stretchable wrapping portion to be positioned around the back of the knee area of an individual; said flexible means having at least one sizing means for tightening or or loosening said flexible means as desired by the individual using the apparatus; a pneumatic chamber attached to said flexible means to be positioned over the kneecap area forming an encircling means around said knee area; said pneumatic area having mesh means for attaching and positioning said pneumatic chamber to said apparatus; said pneumatic chamber further having an aperture located at the center of said pneumatic chamber to be positioned directly over said kneecap to allow freedom of movement of said kneecap; and said pneumatic chamber further having valving means for permitting the inflation or deflation of said pneumatic chamber as desired by the individual using said apparatus.

BRIEF DESCRIPTION OF THE INVENTION

Further objects and features of this invention will become more apparent by reference to the following description taken in conjunction with the accompanying figures, in which:

FIG. 1 is a front elevational view of the novel air pressure knee brace apparatus;

FIG. 2 is a side elevational view thereof;

FIG. 3 is a top plan view thereof; and

FIG. 4 is a cross sectional view taken along line 4—4 of FIG. 1.

DESCRIPTION OF THE PREFERRED EMBODIMENTS

As shown in the figures, the novel air pressure knee brace apparatus 10 comprises a flexible material wrap 11 which fits around the back of the knee. The wrap 11 can be made of a flexible mesh material to improve the cooling characteristics of the apparatus 10. A pair of adjustment straps 12 and 12a that each have buckles 13 and 13a are attached to the flexible wrap 11 to give the user the capability to control the tension of the apparatus 10 around the knee. The adjustment straps could also be tightened or loosened by means of open and closed loop nylon enclosure devices. The front section of the apparatus 10 is composed of a flexible material 14 made of neoprene or the like, that has a pneumatic chamber 15, which is made of latex rubber, and incorporated therein the flexible material 14. The pneumatic chamber has a perimeter of mesh material 16 that is sewn into the neoprene, front flexible material 14 in order to maintain the pre-determined shaped of the pneumatic chamber 15 throughout the different levels of pressure that are maintained by the pneumatic chamber 15 and at the same time hold the pneumatic chamber 15 in predetermined position. A thin layer of mesh can also cover the pneumatic chamber to assist in these purposes. The pneumatic chamber 15 has a valving device 17 that allows the user to build up or release the pressure maintained in the pneumatic chamber 15. The valving device can be constructed in a number of different formats, but the preferred embodiment is a tubular type, pump up valve. An aperture 18 is centered in the pneumatic chamber in order to allow the user to have a free range of motion for the knee while at the same time providing full protection and support for the kneecap or patella.

In use, the individual desiring the support and protection for the kneecap or patella would slide the air pressure knee brace apparatus up into position around the knee with the pneumatic chamber in front of the kneecap. The adjustment straps would then be secured as desired. The air pressure would then be built up through the valve unit. The user would adjust the air pressure to provide as much support and protection and, at the same time, allow as much comfort as desired.

While we have described our invention in connection with specific embodiments thereof, it is clearly to be understood that this is done only by way of example and not as a limitation to the scope of our invention as set forth in the objects thereof and in the appended claims.

We claim:

1. An air pressure knee brace apparatus, for use in providing a lightweight protection and support unit for individuals desiring this protection and support, comprising:

flexible means;

said flexible means comprising a stretchable wrapping portion to be positioned around the back of the knee area of an individual;

said flexible means having at least one sizing means for tightening or loosening said flexible means as desired by the individual using the apparatus;

a pneumatic chamber attached to said flexible means to be positioned over the kneecap area forming an encircling means around the knee area;

said pneumatic chamber having a mesh means for attaching and positioning said pneumatic chamber to said apparatus;

said pneumatic chamber having an aperture located at the center of said pneumatic chamber to be positioned directly over the kneecap to allow freedom of movement of the kneecap; and said pneumatic chamber further having valving means for permitting the inflation and deflation of said pneumatic chamber as desired by the individual using said apparatus.

2. An air pressure knee brace apparatus, according to claim 1, wherein:

said flexible means comprises a neoprene brace that can expand as necessary to enable the apparatus to fit around the leg of an individual.

3. An air pressure knee brace apparatus, according to claim 1, wherein:

said sizing means comprises at least one open and closed loop strapping device to permit tightening and loosening of said apparatus.

4. An air pressure knee brace apparatus, according to claim 1, wherein:

said pneumatic chamber comprises an expandable unit that is attached to said front portion of said flexible means to create an encircling unit around the knee area.

5. An air pressure knee brace apparatus, according to claim 1, wherein:

said mesh means of said pneumatic chamber comprises means for providing the positioning and the desired shape for said pneumatic chamber around the kneecap area;

said mesh means comprises attaching means for attaching said mesh perimeter and said pneumatic chamber to said neoprene brace; and said attaching means comprises stitching means.

6. An air pressure knee brace apparatus, according to claim 1, wherein:

said valving means comprises a valve unit designed to permit the entrance of air pressure, hold air pressure and release air pressure as desired by the individual in order to obtain the optimum support and protection desired by the individual; and said valve unit comprises a bulb assembly.

* * * * *